United States Patent [19]

Cohen

[11] Patent Number: 4,945,103

[45] Date of Patent: Jul. 31, 1990

[54] METHOD OF TREATING PRE-MENSTRUAL SYNDROME

[76] Inventor: Michael Cohen, Kerkeboslaan 4A, Wessenaar, Netherlands

[21] Appl. No.: 297,328

[22] Filed: Jan. 17, 1989

[51] Int. Cl.$^5$ ...................... A61K 31/40; A61K 31/58
[52] U.S. Cl. ...................................... 514/419; 514/171
[58] Field of Search ........................ 424/171, 415, 419

[56] References Cited

U.S. PATENT DOCUMENTS

| | | | |
|---|---|---|---|
| 4,309,415 | 1/1982 | Hurrobin | 514/415 |
| 4,390,531 | 6/1983 | Edgren . | |
| 4,600,723 | 7/1986 | Short | 514/416 |
| 4,654,361 | 3/1987 | Samples | 514/419 |
| 4,665,086 | 5/1987 | Short | 514/416 |
| 4,687,763 | 8/1987 | Wurtman | 514/415 |
| 4,746,674 | 5/1988 | Pierpaoli et al. . | |
| 4,855,305 | 8/1989 | Cohen . | |
| 4,855,313 | 8/1989 | Welch et al. | 514/415 |

OTHER PUBLICATIONS

Frank, *Arch. Neurol. Psychiatr.* 26:1053 (1931).
Abraham et al., *J. Reproductive Med.*, 32:405 (1987).
O'Brien et al., *J. Reprod. Med.*, 30:113 (1985).
Clare, *Can. J. Psych.*, 30:474 (1985).
Bancroft and Backstrom, *Clin. Endocrin.*, 22:313 (1985).
Abraham, *J. Reprod. Med.*, 28:433 (1983).
Abraham, *J. Reprod. Med.*, 32:387 (1987).
Shapiro, *Drugs*, 36:475 (1988).
Cullbert, *J. Acta Psychiatr. Scand.*, 236 (Suppl. 1): 1 (1972).
Dennerstein et al., *Br. Med. J.*, 290:1617 (1985).
Waldhauser et al., *Neuroendocrinology* 39:307 (1984).
Tamarkin et al., *Science*, 227:714 (1985).
Wurtman, *J. Neural Transm.* (Suppl. 21): 1 (1986).
Patkai et al., *Psychosom Med*, 1974; 36:503–512.
Diamond et al., *Compr Psychiatry*, 1976; 17(4); 541–548.
Kashiwagi et al., *Dis Nerv Syst*, 1976; 37:116–119.
Parry et al., *Am J Psychiatry*, 144:6, Jun. 1987.
Clare, *J. Psychom. Res.*, 29(3), 225–233 (1985).
Wetterberg, L., *J. Clin. Endocrinology*, 42:185 (1976).
Hamilton: *Biol. Psychiatry* 24(7), 845–852 (1988).
Johnson, L. Y. et al., *Proc. Soc. Exp. Biol. Med.*, 169, 416 (1982).
Kumar et al., "Testing Nasal Spray Contraceptives in the Rhesus Monkey", 7th Congr. Int. Primatol. Soc., Bangalore 1979, pp. 169–175 (Karger, Basel, 1980).

*Primary Examiner*—Shep K. Rose
*Attorney, Agent, or Firm*—Bernard, Rothwell & Brown

[57] ABSTRACT

A method of treating human females who suffer from pre-menstrual syndrome (PMS) comprises administering melatonin in sufficient doses to relieve the symptoms of PMS.

14 Claims, No Drawings

METHOD OF TREATING PRE-MENSTRUAL SYNDROME

FIELD OF THE INVENTION

This application relates to a method of alleviating the symptoms of pre-menstrual syndrome. More specifically, the application relates to such a method which comprises the administration of melatonin in doses sufficient to alleviate the symptoms of pre-menstrual syndrome.

BACKGROUND OF THE INVENTION

The pre-menstrual syndrome (PMS) in women is a medical condition characterized by a number of both somatic and psychological symptoms. The condition first was described by Frank, *Arch. Neurol. Psychiatr.* 26:1053 (1931). The symptoms of PMS are associated with a woman's menstrual cycle and appear only during that portion of her menstrual cycle which follows ovulation. Thus, PMS is a syndrome of the luteal phase of the menstrual cycle.

PMS is a chronic condition, and women who suffer from it typically experience it with each cycle during the fertile phases of their lives, i.e., between the first menstrual cycle (the menarche) and the last menstrual cycle, a period of time after which a woman enters menopause. Fluctuations from cycle to cycle in the severity of PMS frequently occur, however, with some months being associated with significantly more difficulties than others. The intensity of the manifestations of the syndrome also can vary from year to year, as a woman passes through different phases in her reproductive life.

Typically, a woman ovulates each month during the reproductive phase of her life. Thus, PMS can be a significant disability for many years of a woman's life. PMS has a profound effect on the working capacity of afflicted women and can cause the loss of many days of work over a woman's lifetime. It has been estimated that the cost of lost working days due to PMS in the United States alone exceeds ten billion dollars annually. In addition, PMS can lead to marital and family problems and cause intense suffering on the part of those who suffer from it.

As noted above, the timing of symptoms of PMS coincides with a certain part of a woman's menstrual cycle. Typically, the condition is manifested after ovulation (i.e., during the luteal phase of the menstrual cycle) and is intensified as the woman approaches the onset of menstruation. Most commonly, the symptoms are most pronounced during the last seven to ten days of the luteal phase of her cycle, that is, the last seven to ten days prior to the onset of her menstrual bleed. Once the menstrual blood loss has begun, the symptoms abate and the condition of the patient improves.

The most common somatic symptoms of PMS include swelling and tenderness of the breasts, abdominal pain, pelvic pain and cramps, pain in the iliac fossa, feelings of bloatedness and weight gain, diminished activity, efficiency and performance, perspiring, skin lesions, edema, vertigo and diarrhea or constipation. Less common symptoms include sore eyes, joint pain, asthma and epilepsy.

The most common psychological symptoms include irritability, agitation, anxiety, confusion, fatigue, mental depression, lethargy, insomnia or hypersomnia, decreased libido, loss of confidence and judgment, suicidal ideation, accident proneness, loss of concentration and attention span and the development of food cravings, especially for sweets, such as chocolate.

The combination of the somatic and psychological symptoms which can be experienced by one suffering from PMS can lead to social isolation, a poor ability to function in the workplace and home and difficulties in relating to family members According to some physicians, PMS best can be classified as a number of distinct subsyndromes dependent upon the clustering of symptoms characteristic of the classified subject. See Abraham, *J. Reproductive Med.* 32(6):405 (1987). In this system of classification of PMS (termed PMTS for pre-menstrual tension syndromes) the following subtypes exist:

(a) PMT-A: symptoms primarily include anxiety, irritability and nervous tension, which progress in time from mid-cycle to menstruation and frequently are associated with a depressive mood change.

(b) PMT-H: predominant symptoms include premenstrual sensation of weight gain, abdominal bloating and tenderness, breast congestion and mastalgia and occasionally, minimal edema.

(c) PMT-C: in this subgroup, the primary symptom is an increased appetite in the luteal phase of the menstrual cycle. The food craving and hunger primarily are directed toward refined sugars. The food craving frequently is associated with emotional tension.

(d) PMT-D: this subsyndrome primarily is characterized by intense states of confusion, social withdrawal and suicidal ideation. The patients also may experience shifts in their energy levels, with some becoming lethargic and others becoming very excitable. Many of these patients complain of difficulties in verbalization.

The etiology of PMS is not well understood. A number of conflicting theories have been proposed to explain the condition. Despite fifty years of intensive research, however, most authorities agree that no definitive etiology and pathophysiology have been elucidated for this complex physical condition.

In view of the fact that PMS is associated with the menstrual cycle, many theories are based on the assumption that the condition is related to a basic "endocrine imbalance" in the women who suffer from the syndrome. Attention has been focused especially upon ovarian hormones. Some scientists have considered a progesterone deficiency to play a role in PMS, while others have related the condition to an excess of estrogens or androgens. Others have thought the endocrinological aberration to be related to adrenal cortex hormones, such as corticosteroid (hydrocortisone) or mineral corticoids (aldosterone).

In yet other theories, mastalgia and fluid retention were thought to be related to pituitary dysfunction and specifically to an excessive secretion of the hormone prolactin. Some studies have considered the basic dysfunction associated with PMS to be related to prostaglandin secretion and metabolism. Other theories have considered a serotonin deficiency syndrome and a hypothesized "neuro-endocrine imbalance."

Other scientists have related PMS to a nutritional deficiency in either vitamin B-complex, especially vitamin B-6 (pyroxidine), or essential fatty acids, especially linolenic acid. Others have put forth the "yeast overgrowth syndrome" which was thought to be the outcome of pu candida albicans' overgrowth with associated production of "toxins." Some additional studies have looked for various food allergies and respiratory allergies as an explanation of PMS.

Reviews summarizing these various theories include O'Brien, P., *J. Reprod. Med.* 30(2): 113 (1985); Claire, A., *Canadian J Psych.* 30(7):474 (1985); Bancroft, J. and T. Bachstrom, *Clin. Endocrin.* 22:313 (1985); Abraham, G. E., *J. Reprod. Med.* 28(7):433 (1987); and Abraham, G. E., *J. Reprod. Med.* 32(6):387 (1987).

Despite all these efforts, no definite etiology has been determined. As a result, treatment of PMS has taken numerous forms and has reflected the wide variety of theories of its cause. Most commonly, the treatment of PMS has been treated through the administration of nonsteroidal, anti-inflammatory drugs, including aspirin, naparoxen, indomethacin, mefenamic acid, ibuprofen and piroxicam. See Shapiro, S. S. *Druqs* 36:475 (1988).

In other treatment modalities, physicians have prescribed psychoactive drugs, such as lithium carbonate, benzodiazepines, and tricyclic antidepressants, and frequently have combined them with intensive psychiatric treatment.

Still other treatment modalities have been focused on efforts to correct the poorly understood "endocrine imbalance" through the administration of various contraceptive medication combinations. Unfortunately, however, many women have reported that taking the oral contraceptives have made them feel worse. See Cullberg, J. *Acta Psychiatr. Scand.* 236(supp. 1):1 (1972). Other endocrine treatments have involved the administration of progesterone in the luteal phase of the menstrual cycle; for example, 100 mg progesterone administered each morning and 200 mg administered each evening have been found to have a significant benefit for women with PMS. See Dennerstein et al., *Br. Med. J. (Clin. Res.)* 290(6482): 1617 (1985). In other treatments, depot methoxyprogesterone has been administered and reported to be effective. Treatment with progesterone has a limited value, however, in that most of the symptoms of PMS do not disappear upon its administration.

Other treatment methods that have been tried include endocrine management of the condition through the treatment with thyroid hormone medication; bromocriptine administration to reduce the synthesis and secretion of prolactin; and danazol administration to inhibit multiple enzymes involved in ovarian steroidogenesis and prevent the midcycle LH surge. This last method of treatment is effective in some patients; however, it carries with it the risk of estrogen withdrawal and early climacteric symptoms. It also can cause osteoporosis in long term users.

In view of the drawbacks and inadequacies with existing methods of treating PMS, new therapies are sought. Accordingly, it is an object of the present invention to provide a method for effectively alleviating the symptoms of PMS. It is a further object of this invention to provide such a method that is attended by a minimum of negative side effects.

SUMMARY OF THE INVENTION

In accordance with the method of this invention, a method of alleviating the symptoms of PMS comprises administering melatonin to a human female of childbearing years who suffers from symptoms of PMS, the melatonin being administered in doses sufficient to alleviate the symptoms. In one embodiment of the invention, a progestogen can be administered in combination with the melatonin.

DETAILED DESCRIPTION OF THE INVENTION

The present invention is based upon the unexpected discovery that the administration of melatonin (N-acetyl-5-methoxytryptamine) to women in daily dosages on a cyclic schedule, preferably during the luteal phase of their menstrual cycles, results in the substantial reduction of the symptoms of PMS. It further has been discovered that when melatonin is combined with a progestogen, such as norethisterone or micronized progesterone capsules, the effects of the melatonin are enhanced and the symptoms of PMS essentially disappear, even in patients who previously had been therapy resistant.

Melatonin is a hormone synthesized and secreted by the pineal gland. The exact role of the hormone has not yet been determined. Exogenous melatonin administration in humans has been studied in conjunction with a hypothesis that an abnormal melatonin rhythm is associated with endogenous depression and for pharmokinetic purposes (Waldhauser, F., *Neuroendocrinology* 39:307 [1984]) and in connection with sleep-wake rhythms and the phenomenon of "jet-lag" following airplane trips associated with a change in time zones. Recently, it has been discovered that pharmacological doses of melatonin administered daily to a human female of child-bearing years suppresses the normal mid-menstrual cycle surge in leutinizing hormone sufficient to prevent ovulation. The use of melatonin as a contraceptive is described in U.S. Pat. application Ser. No. 029,229, filed Mar. 23, 1987.

Although not wishing to be bound by theory, it appears that women who suffer from PMS also suffer from a condition known as hypomelatoninemia, which probably is responsible, at least in part, for the development of PMS. If this is true, women suffering from PMS do not experience a normal, symptom-free menstrual cycle due to an insufficiency of melatonin and, probably, also to a sensitivity to the lack of this hormone. Although the mechanism of action of melatonin in reducing or eliminating PMS in women is not fully understood, it probably is achieved through an inhibition of the follicular growth in the ovaries. Thus, the reduction in follicle development is associated with a lessened hypothalamic, pituitary, and ovarian hormone production which in turn is linked directly to, and is responsible for, the development of PMS. Alternatively, there is a possibility that melatonin affects the membrane and cytoplasmic receptors for the various sexual hormones which play a role in the follicular growth, follicular rupture, and the ovulatory process and corpus luteum development.

It has been found that the administration of melatonin to women, preferably during the luteal phase of their cycles, leads to a substantial reduction in, and in some instances, the disappearance of, the symptoms of PMS. Preferably, the melatonin is administered on each of the last three to fourteen days of the cycle, i.e., the three to fourteen days immediately preceding the onset of menstrual blood loss. Generally, the melatonin is administered in amounts ranging from about 2 mg. to about 2000 mg. per day. Preferably, from about 30 mg. to about 300 mg. are administered per day. The amount provided in each daily dosage can vary with the method of administration selected.

Desirably, the melatonin is administered for the minimum number of days necessary to achieve a substantial reduction or elimination of the symptoms of PMS. Often, it is necessary to administer the melatonin only on those days of a woman's cycle in which she is experiencing symptoms of PMS. For example, if a woman suffers from PMS only during the last four days of her cycle prior to the onset of her menstrual bleed, it may be sufficient to administer melatonin in the daily dosage levels indicated above only during those four days of her cycle. If this should prove to be insufficient to alleviate her symptoms, however, the melatonin additionally can be administered during one or more days immediately preceding the onset of her symptoms. In certain cases, it may be desirable to administer the melatonin during every day of the luteal phase of the patient's cycle.

In an alternative embodiment of this invention, a woman suffering from PMS can be treated with small daily dosages of melatonin during a portion of, or throughout, the follicular phase of her cycle as well as during the luteal phase for a maximum of about 21 or even 28 (i.e., continuously throughout the cycle) consecutive daily doses. Such a regimen of administration acts to partially suppress the hormonal output which is associated with the follicular phase of her cycle and ultimately results in the hormonal profile which is theorized to be a causative agent of PMS. In this embodiment of the invention, the dosages generally vary between about 2 mg. and about 300 mg. per day, preferably between about 2 mg. and 100 mg. per day, throughout the cycle.

Surprisingly, it also has been found that a side benefit of administering melatonin in dosages and regimens sufficient to prevent ovulation, as described in U.S. Pat. application No.029,229, referenced above, can be the alleviation of symptoms of PMS. Thus, in another embodiment of this invention, melatonin can be administered in about 5 to about 14 daily dosages immediately preceeding a woman's normal day of ovulation. Ovulation typically occurs on the fourteenth day of a woman's cycle or between the ninth and seventeenth day of her cycle. In this embodiment, the melatonin typically is administered in dosages of about 2 to about 500 mg per day, preferably about 30 to about 300 mg. per day. Although the underlying theory is not fully understood, it appears that the administration of such a regimen of melatonin can serve to correct an existing hormonal deficiency and restore hormonal equilibrium, thus alleviating the symptoms of PMS. This result does not appear to be related to the blocking of ovulation, as the administration of conventional contraceptives has been found to aggravate the symptoms of PMS in some women.

The melatonin can be administered to women orally, parenterally or in the form of an implant. Administration is most convenient when the melatonin is in oral dosage form, such as capsules, tablets, suspensions or solutions. Capsules or tablets are preferred. Capsules can be prepared by mixing the compound with a pharmaceutically acceptable excipient and then filling gelatin capsules with the mixture in accordance with conventional procedures. Alternatively, the melatonin can be mixed with one or more lubricants, such as stearic acid or magnesium stearate, flavor ameliorating agents, disintegrating elements, including potato starch and alginic acid, binders, such as gelatin and corn starch, and/or tablet bases, including lactose, corn starch and sucrose, and then pressed into tablets.

As an alternative to oral administration, the melatonin can be administered parenterally or in the form of an implant. For parenteral administration, the melatonin is provided in injectable doses of a solution or suspension of the hormone in a physiologically acceptable diluent with a pharmaceutical carrier. The carrier can comprise water or an oil and optionally also can contain a surfactant or other pharmaceutically acceptable adjuvant. Suitable oils include those of animal, vegetable, petroleum or synthetic origin, including peanut, soybean, corn, sesame, castor and mineral oil. Preferred liquid carriers include water, saline, aqueous sugar solutions, and glycols, such as propylene glycol or polyethylene glycol.

The melatonin can be administered in the form of an implant, which is formulated such that it will provide a sustained release of the melatonin over time. To make the implant, the melatonin can be compressed into small cylinders and placed inside a physiologically acceptable shell material such as a biodegradable or porous polymer in accordance with conventional implant technology. Similarly, the melatonin can be administered in the form of a suppository, which also will provide for the sustained release of the melatonin over time. The melatonin can be mixed with a conventional suppository base, i.e., a physiologically acceptable material which is meltable at body temperature.

Inasmuch as in a preferred embodiment of this invention the melatonin is administered daily only for a portion of a female's cycle following her day of ovulation, it may be advisable to administer the melatonin in sequential combination with a placebo to make it easier for the woman to remember when to take the melatonin. That is, a placebo could be administered on each day of a woman's cycle for a prescribed number of days, beginning on the first day after the cessation of bleeding from her last menstrual cycle. Then, the melatonin is administered for a prescribed number of days of the woman's cycle, until the onset of her next menstrual bleeding.

In any of the embodiments of the invention described above, the melatonin cand be administered in combination with a progestogen. As noted above, the administration of a progestogen alone has been found to be an effective form of treatment of PMS in some women. It now has been found that administration of a progestogen in combination with melatonin provides a particularly effective form of treatment. Any progestationally active compound is suitable for use in the present invention. Suitable progestogens include progesterone and derivatives thereof. The presently preferred progestogen is norethisterone (i.e., 19-nor-17α-ethynyl-17β-hydroxy-4-androsten-3-one) and norgestrel (13β-ethyl-17α-ethynyl-17β-hydroxygon-4-en-3-one). Other progestogens include the chlormadinone-acetate (6-chloro-17-hydroxy-pregna-4,6-diene-3,20-dione acetate), norethynodrel (17α-ethynyl-17-hydroxy-estr-5(10)-en), medroxyprogesterone acetate (17α-acetoxy-6α-methyl-pregn-4-ene-3,20-dione), megestrol acetate (17α-acetoxy-6-methyl-pregna-4,6-diene-3,20-dione), lynestrenol (17α-ethynyl-17β-hydroxy-estr-4ene), quingestrone (3-cyclopentyloxy-pregna-3,5-diene-20one), norethindrone acetate (17β-acetoxy-17α-ethnyl-estr-4-en-3-on), ethynodiol acetate (3β, 17β-diacetoxy-17α-ethynyl-estr-4-ene), dimethisterone [17β-hydroxy-6α-methyl-17(-1-propynyl)-androst-4-en-3-one], and levonorgestrel.

When the melatonin is administered in combination with a progestogen, the dosage of melatonin can be lower than typically administered in the absence of the progestogen, i.e., the dosage of melatonin generally is within the range of about 7.5 mg to about 125 mg. per day. The actual amount of progestogen provided in each daily dosage will depend upon the particular progestogen chosen, its relative potency, and the method of administration selected. For example, a lesser quantity of a more potent progestogen may achieve the same results as a larger quantity of a less potent progestogen. For example, if the progestogen to be administered is norethisterone, it generally is administered in the range of from about 25 μg. to about 750 μg. per day. If another progestogen is to be administered, the amount provided desirably is such that its potency is approximately equivalent to the potency of an amount of norethisterone within the stated range. The desired dosage of a given progestogen within these guidelines can be determined easily by a person with skill in the art. As noted above, the amount of progestogen also can vary with the mode of administration, with lower doses typically needed for administration of an implant or intravenous injection than for oral administration.

If the melatonin is administered in combination with a progestogen, the two active components conveniently are physically combined and administered together, although they also can be administered separately.

In a preferred embodiment of this invention, the compositions of the invention are administered in oral dosage form, preferably in the form of pills or capsules. The pills or capsules can be packaged in any manner suitable for proper delivery and use. Preferably, they are packaged in the form of a pharmaceutical kit or package in which the daily unit dosage forms are provided or arranged in a contiguous, sequential order which will enable the woman taking the pills to take the pills at the appropriate time in her reproductive cycle. Suitable kits or packages include the conventional oral contraceptive bubble plastic package containing individual bubbles for the number of pills to be taken during the woman's cycle in a sheet of flexible plastic. The bubbles are sealed by a sheet of plastic which can break and release a pill when the bubble is pressed. On the first day of medication, the first pill in the sequence, whether it contains melatonin (or a combination of melatonin and a progestogen) or a placebo, is removed from its individual slot in the package and taken. The next pill in the sequence is taken the next day and so on thereafter until the dispenser is empty. A new dispenser is begun on the appropriate day of her next cycle. Appropriate notations or instructions can be placed on the dispensing kit to guide or instruct the user in the proper use of the medication.

The present invention is further described and illustrated by the following examples, which are provided for informational purposes only and are not to be construed as limiting.

EXAMPLE I

A 26 year old woman had symptoms of PMS which included severe irritability, lethargy, and depression in the last 10 days of her menstrual cycle. The symptoms worsened as she approached the first day of her menstrual cycle to the point that she had bouts of suicidal ideation, crying, irrational behavior and aggression. She was given melatonin in doses of 100 mg. per day from day 16 of her menstrual cycle through day 28. Her symptoms of PMS were considerably lessened; while some lethargy persisted, her emotional lability and symptoms of depression disappeared.

EXAMPLE II

A 24 year old woman with severe symptoms of PMS, including feelings of bloatedness, breast pain, pelvic discomfort, craving for sweet foods and depression, was administered 125 mg. of melatonin per day beginning on day 18 of her cycle and continuing through day 28. The symptoms improved significantly, but they did not disappear. Increase of the dosage to 250 mg per day did not further lessen her symptoms. A new medication schedule was prescribed which comprised a combination of 500 per day of norethisterone and 125 mg per day of melatonin. The medication was prescribed for the last ten days of her menstrual cycle (day 18 through day 28). This time, the medication administration resulted in a complete disappearance of all of her symptoms.

EXAMPLE III

A 33 year old woman with a long history of PMS was medicated with 300 mg of melatonin daily on a continuous basis for two months and all symptoms abated. After two months her cycle lost its regularity; that is, the medication prolonged the follicular phase and shortened the luteal phase of her cycle. As a result, her cycle changed from a regular 26 day cycle to 37 days, followed by cycles of 41, 52 and 40 days. The patient, however, felt no premenstrual tension and did not experience any negative side effects with the medication.

Endocrine measurements were performed during the cycle on a regular basis. They demonstrated that follicular growth was slightly suppressed, the patient's estrogen level was slightly suppressed and her follicle stimulating hormone (FSH) also was low (not higher than 6nmol/l). In addition, the normal surge in leutinizing hormone (LH) was suppressed. Progesterone levels were below 30 nmol/l, which is lower than in a regular cycle.

EXAMPLE IV

In another study, melatonin was administered to a 27 year old woman whose symptoms of PMS included premenstrual tension, irritability, breast pain and lower back pain. Melatonin was administered at 300 mg. per day from day 7 through day 17 of her cycle. This was found to reduce significantly all of her symptoms of PMS as described above. In addition, upon administration of melatonin, the woman's craving for sugars and chocolate, which frequently was associated with severe head aches, disappeared. Blood values were depressed for FSH, LH, estradiol and progesterone. The patient's follicular growth was slightly depressed but the follicular phase of her cycle was prolonged.

I claim:

1. A method of alleviating premenstrual anxiety, irritability, depression, confusion, fatigue, insomnia, hypersomnia, weight gain, abdominal bloating, pain or tenderness, breast swelling or tenderness, pelvic pain or cramps, increased appetite or weight gain, edema, or a combination thereof which comprises the administration, on a cyclic schedule, of melatonin in a series of daily doses to a human female of child-bearing years who suffers symptoms of PMS, said administration at dosage levels sufficient to alleviate said symptoms.

2. A method in accordance with claim 1 wherein the melatonin is administered in about 3 to about 14 daily doses during the luteal phase of the female's menstrual cycle immediately preceding the onset of the female's menstrual bleed.

3. A method in accordance with claim 2 wherein the daily dosage level is in the range of about 2 mg. to about 2000 mg per day.

4. A method in accordance with claim 3 wherein the daily dosage level is in the range of about 30 mg. to about 300 mg. per day.

5. A method in accordance with claim 1 wherein the melatonin is administered on each day of the luteal phase and at least some days of the follicular phase of the female's menstrual cycle.

6. A method in accordance with claim 5 wherein the daily dosage level is in the range of about 2 mg. to about 300 mg.

7. A method in accordance with claim 6 wherein the daily dosage level is in the range of about 2 mg. to about 100 mg.

8. A method in accordance with claim 1 wherein the melatonin is administered in about 3 to about 14 daily doses immediately preceding the female's normal day of ovulation.

9. A method in accordance with claim 8 wherein the daily dosage level is in the range of about 2 mg. to 500 mg.

10. A method in accordance with claim 9 wherein the daily dosage level is in the range of about 30 to about 300 mg.

11. A method in accordance with claim 1 wherein the method of administration is oral.

12. A method in accordance with claim 1 wherein the method of administration is intravenous injection in a physiologically suitable carrier.

13. A method in accordance with claim 1 wherein the method of administration is through an implant.

14. A method in accordance with claim 1 wherein the method of administration is through a suppository.

* * * * *